United States Patent [19]

O'Leary et al.

[11] Patent Number: 5,120,656
[45] Date of Patent: * Jun. 9, 1992

[54] PROCESS FOR DEBRIDING BONE

[75] Inventors: Robert K. O'Leary, Spring Lake; Annamarie B. Prewett, Fairhaven, both of N.J.

[73] Assignee: Osteotech, Inc., Shrewsbury, N.J.

[*] Notice: The portion of the term of this patent subsequent to Aug. 7, 2007 has been disclaimed.

[21] Appl. No.: 560,661

[22] Filed: Aug. 3, 1990

Related U.S. Application Data

[63] Continuation-in-part of Ser. No. 395,782, Aug. 18, 1989, Pat. No. 4,946,792.

[51] Int. Cl.$^5$ .............................................. A01N 1/02
[52] U.S. Cl. .................................. 435/268; 435/267; 435/1; 623/16
[58] Field of Search .......................... 435/267, 268, 1; 623/16

[56] References Cited

U.S. PATENT DOCUMENTS 4,399,123  8/1983  Oliver et al. .
4,642,292  2/1987  Reid et al. .
4,656,137  4/1987  Balassa .
4,801,451  1/1989  Hellgren et al. .

OTHER PUBLICATIONS

Tobiume–Chem. Abst. vol. 90 (1979), No. 12274p.

Primary Examiner—Sam Rosen
Attorney, Agent, or Firm—Dilworth & Barrese

[57] ABSTRACT

Bone is enzymatically debrided prior to undergoing further processing which renders the bone suitable for osteoprosthetic use.

21 Claims, No Drawings

# PROCESS FOR DEBRIDING BONE

CROSS REFERENCE TO RELATED APPLICATION

This application is a continuation-in-part of copending U.S. patent application Ser. No. 07/395,782, filed Aug. 18, 1989, now U.S. Pat. No. 4,946,792.

BACKGROUND OF THE INVENTION

This invention relates to a process for debriding bone and is principally concerned with the removal of the periosteum, a specialized connective tissue made up largely of collagen type material which covers all bones of the body, as well as other tissues associated with bone, e.g., muscle, cartilage and/or tendons, as a preliminary step in the processing of bone which is intended for osteoprosthetic use.

Bone and related tissue referred to as allografts, hereinafter collectively referred to as "bone" for the sake of convenience, are used in numerous surgical specialties to repair or replace defective or damaged bones. The range of allograft transplants includes entire joints, sections of long bone, bone chips for surgical procedures such as spinal fusion and craniotomies and bone dust used in dental repair/reconstruction.

Prior to use in osteoprosthetic surgery, harvested bone tissue may be processed by any of a variety of procedures, e.g., defatting, demineralization, reshaping, and the like, which prepare the bone for grafting or implantation. As a necessary preliminary to these and other bone tissue processing techniques, the periosteum must be removed, a procedure referred to herein as "debridement". Up until now, it has been the practice to accomplish debridement of bone by purely mechanical techniques, a time-consuming, labor-intensive procedure which adds significantly to the cost of bone tissue intended for osteoprosthetic use.

SUMMARY OF THE INVENTION

It is a principal object of the invention to provide a process for the debridement of bone employing one or more enzymes which loosen the periosteum facilitating its removal from the bone.

It is another object of the invention to provide such an enzymatic debridement process employing a permeation enhancer to provide more effective penetration of the enzyme(s) and, optionally, one or more other substances such as disinfectants and antibiotics, into the periosteum.

It is yet another specific object of the invention to remove enzymatically loosened periosteum from bone employing a high velocity fluid stream, e.g., of water.

In keeping with these and other objects of the invention, there is provided a process for the debridement of harvested bone having its periosteum intact which comprises contacting the periosteum with a solution of enzyme selected from the group consisting of proteolytic enzyme, collagen-digesting enzyme and mixtures thereof under enzyme activity-promoting conditions for a period of time sufficient to loosen the periosteum from the underlying bone surface and thereafter removing the loosened periosteum from the bone.

In addition to significantly reducing the time required to effect debridement compared with that required for the older mechanical methods, the enzymatic debridement process of this invention greatly facilitates the removal of periosteum from areas which are difficult to reach with mechanical debridement devices such as scalpels and curettes. Thus, in addition to providing a relatively rapid process of bone debridement, the process of the present invention greatly facilitates the removal of periosteum and related connective tissue such as cartilage, tendons and ligaments from areas of bone which undergo mechanical debridement only with particular difficulty.

DESCRIPTION OF THE PREFERRED EMBODIMENTS

Any proteolytic enzyme(s), collagen-digesting enzyme(s) or combination of proteolytic enzyme(s) and collagen-digesting enzyme(s) which effect the loosening of the periosteum can be used herein. Suitable proteolytic enzymes include ficin, pepsin, trypsin, chymotrypsin, papain, elastase and the like, with trypsin being preferred. Suitable collagen-digesting enzymes include collagenase, which is preferred, and stromelysin. A particularly suitable combination of enzymes contains one or more proteolytic enzymes such as trypsin, chymotrypsin and/or elastase, and the collage-digesting enzyme collagenase.

It is within the scope of this invention to contact the periosteum-sheathed bone with enzyme solution in a sequence of steps, first contacting the periosteum with a first enzyme solution containing proteolytic enzyme(s) or collagen-digesting enzyme(s), separating the bone from the first enzyme solution and thereafter contacting the bone with its periosteum still somewhat intact with a second enzyme solution containing either collage-digesting enzyme(s) if proteolytic enzyme(s) were present in the first enzyme solution or proteolytic enzyme(s) if collagen-digesting enzyme(s) were present in the first enzyme solution. However, it is ordinarily preferred to contact the periosteum of the bone with a single enzyme solution containing both types of enzymes in a single contacting step.

The enzyme(s) must, of course, be employed under conditions which permit or promote their enzymatic activity. For example, in the case of papain, the temperature can be anywhere in the range of from about ambient to about 70° C., preferably from about 25° to about 55° C., and the pH can be within the range of from about 3 to 9, preferably from about 4 to about 7. In the case of trypsin, similar temperature ranges are appropriate and the pH is preferably set at about 8 to 9 for optimum activity Collagenase is active under similar conditions.

The enzyme or enzyme mixture is dissolved in water and/or other suitable carrier, preferably one which is sterile such as sterile physiological saline. The total amount of enzyme can vary widely provided, of course, an effective amount of enzyme is employed. Optimum amounts of proteolytic and/or collagen-digesting enzyme can be readily determined employing simple and routine experimental procedures. The enzyme solution can contain a variety of additives including organic and inorganic salts, gel-forming materials, antimicrobials, surface active agents, and the like.

In general, contact times of the bone with the enzyme solution on the order of from about 30 minutes to several hours or even days will effect a degree of loosening of the periosteum which greatly facilitates its removal from the underlying bone.

It can also be advantageous to accomplish debridement employing a stream of high velocity fluid to remove the enzymatically loosened periosteum from the surface of the bone. A high velocity stream of sterile water or physiological saline is preferably utilized for this purpose and its application follows the soaking of the bone in the enzyme solution for the contact times mentioned above.

If desired, the debridement process herein can be accompanied by exposure of the bone to sterilizing ultraviolet radiation (e.g., of 254 millimicrons wavelength). Such exposure can be achieved in a variety of ways, e.g., by placing the bone in an environment suffused with ultraviolet radiation or by localized application of ultraviolet radiation upon the surface of the enzymatically loosened periosteum while the periosteum is undergoing removal from the bone. When, e.g., a high velocity stream of water is used to effect such removal, one or more optical fibers coincident with the longitudinal axis of the stream and preferably positioned within the central portion thereof delivers ultraviolet radiation to the surface of the periosteum simultaneously with the impingement of the stream thereon.

In accordance with a particular embodiment of the enzymatic bone debridement process herein, an enzyme penetration or permeation enhancer is included in the enzyme debridement solution to enhance penetration or diffusion of the enzyme into the periosteum or to otherwise accelerate the loosening of the periosteum from the underlying bone. Suitable penetration or permeation enhancers include surface active agents which may be of the cationic, non-ionic, anionic or amphoteric variety; glycerol monolaurate; hexamethylene lauramide; dimethyl formamide; propylene glycol; diethyltoluamide; N-methyl-1-2-pyrrolidone; declymethylsulfoxide; benzyl alcohol; dimethyl sulfoxide; alkyl-N-N-dialkyl-substituted amino acetates; lecithin; dimethylacetamide; laurocapram; dodecyl-L-pyroglutamate; 1-oxohydrocarbyl-substituted azacyclohexanes; azone; hydroxyethyl acetamide; tetrahydrofurfuryl alcohol; methyl laurate; isopropyl palmitate; isopropyl myristate; isopropyl stearate; and, enamines. Preferred permeation enhancers are isopropyl palmitate and isopropyl myristate. The amount of permeation enhancer employed can vary widely with quantities of from about 0.01 to about 10 weight percent of enzyme debridement solution being effective in most cases.

The enzyme debridement solution can also contain one or more other components which are generally beneficial to the process, e.g., antibiotics and/or disinfectant agent(s). Antibiotics which can be employed include bacitracin, polymyxin B sulfate, erythromycin, neomycin, penicillin, tetracyclines, viomycin, chloromycetin, cefazolin, ampicillin, tobramycin, clindamycin, and gentamicin. Disinfectant(s) which can be employed in accordance with the present invention are generally present in an aqueous solution and are administered in an effective disinfecting amount Examples of disinfectants which can be employed include ethylene oxide, propylene oxide, ethanol, hydrogen peroxide (preferably as 10% hydrogen peroxide in aqueous solution), chlorine dioxide, chlorahexidene gluconate, glutaraldehyde, formaldehyde, peracetic acid (hydrogen peroxide and acetic acid in aqueous solution), povidone iodide (polyvinylpyrrolidone), sodium hypochlorite, quaternary ammonium compounds, cetyl alcohol and benzalkonium chloride. A preferred disinfectant is an aqueous ethanol solution. Optimum amounts of these and other optional components of the enzyme debridement solution can be readily determined employing routine experimentation.

The following examples are illustrative of the bone debridement process of the present invention

EXAMPLE 1

This example illustrates the enzymatic debridement process of this invention employing a proteolytic enzyme, trypsin, alone.

A section of femoral bone which has been harvested under aseptic conditions in accordance with accepted practice and from which the soft tissue has previously been removed is placed in a physiological saline solution of commercial trypsin (TRYPURE, Novo Industri, Copenhagen, Denmark) assaying approximately 0.001 enzyme units per mg. The temperature is maintained at about 25° C. and the pH at a level of about 8. After a period of 4 hours, the periosteum is found to be loosened from the bone and is easily removed therefrom.

EXAMPLE 2

This example illustrates the enzymatic debridement process of this invention employing a collagen-digesting enzyme, collagenase, alone.

To a solution containing 50 mM phosphate buffered saline (pH=7.8) and 0.4 mM calcium chloride, collagenase obtained from *Clostridium histolyticum* was added to effect a final concentration of 0.5 mg/ml. A sufficient volume of this solution was used to fully submerge an adult femur with an intact periosteum. The digestion took place without agitation for a period of 50 minutes at a temperature of 34.1° C. The bone was removed from the solution and, using forceps, the by-now softened periosteum could be readily dislodged from the bone. The femur was placed back in the solution and allowed to digest without agitation at 34.1° C. for a period of 12 hours. Following period of digestion, the periosteum had dislodged completely from the bone.

EXAMPLE 3

This example and the example which follows illustrates the enzymatic debridement process of this invention employing a combination of proteolytic and collagen-digesting enzymes.

To an aqueous solution of 50 mM phosphate buffered saline (pH=7.8) and 0.5 mM calcium chloride, collagenase from *Clostridium histolyticum* was added to effect a final concentration of 0.1 mg/ml. Trypsin was then added at a final concentration of 0.1 mg/ml. A human right proximal tibia from which most of the muscle and tendon attachments had ben previously removed was submerged in the protease solution described above and digested for a period of one hour at 37° C. Following the digestion period, the periosteum could be easily dislodged from the bone.

EXAMPLE 4

A solution of 1.0 g sodium tripolyphosphate in 100 ml distilled water was prepared. The proteases alpha chymotrypsin (1.5 mg) and elastase (2.5 mg) were added to the solution. A human right proximal tibia from which most of the muscle and tendon attachments had been previously removed was placed in this solution for one hour at 25° C. The solution was separated from the bone and the bone was subsequently submerged for one hour at 37° C. in a 50 mM phosphate buffered saline solution (pH=7.8) containing 0.4 mM calcium chloride containing collagenase from *Clostridium histolyticum* at a final concentration of 0.1 mg/ml. After these treatments, the periosteum and remaining muscle tissue was easily dislodged from the bone.

What is claimed is:

1. A process for the debridement of harvested bone having its periosteum intact which comprises contacting, the periosteum with a solution of at least one collagen-digesting enzyme under enzyme activity-promoting conditions for a period of time sufficient to loosen the periosteum from the underlying bone surface and thereafter removing the enzymatically loosened periosteum from the bone.

2. The process of claim 1 wherein the collagen-digesting enzyme is selected from the group consisting of collagenase, stromelysin and mixtures thereof.

3. The process of claim 1 wherein the temperature of contacting ranges from about 20° C. to about 70° C.

4. The process of claim 1 wherein the temperature of contacting ranges from about 25° to about 55° C.

5. The process of claim 1 wherein the pH ranges from about 3 to 9.

6. The process of claim 1 wherein the contact time of the periosteum with the enzyme solution is at least about 30 minutes.

7. The process of claim 1 wherein the enzyme solution is a sterile physiological saline solution.

8. The process of claim 1 wherein the enzyme solution contains a permeation enhancer.

9. The process of claim 8 wherein the permeation enhancer is a surface active agent.

10. The process of claim 1 wherein the enzyme solution contains at least one member of the group consisting of antibiotic and disinfectant.

11. The process of claim 10 wherein the disinfectant is ethanol.

12. The process of claim 1 wherein the enzyme solution contains a permeation enhancer and at least one member of the group consisting of antibiotic and disinfectant.

13. The process of claim 1 wherein the enzyme solution contains an enzyme permeation enhancing amount of at least one enzyme permeation enhancing surface active agent and a disinfecting amount of ethanol.

14. The process of claim 1 wherein the enzymatically loosened periosteum is removed from the bone by the impact of a high velocity fluid stream directed against the periosteum.

15. The process of claim 14 wherein the high velocity fluid stream is water or physiological saline.

16. The process of claim 1 wherein removal of the enzymatically loosened periosteum from the bone is accompanied by exposure of the bone to sterilizing ultraviolet radiation.

17. The process of claim 15 wherein removal of the enzymatically loosened periosteum from the bone is accompanied by exposure of the bone to sterilizing ultraviolet radiation directed against the surface of the periosteum upon which the high velocity fluid stream impinges.

18. The process of claim 1 wherein the periosteum-containing bone is contacted with a solution of proteolytic enzyme before, during or following contact of the periosteum with the solution of collagen-digesting enzyme.

19. The process of claim 18 wherein the proteolytic enzyme is present in the solution of collagen-digesting enzyme.

20. The process of claim 18 wherein the collagen-digesting enzyme is collagenase.

21. The process of claim 19 wherein the collagen-digesting enzyme is collagenase.

* * * * *